United States Patent [19]

Müller et al.

[11] 4,322,419
[45] Mar. 30, 1982

[54] BICYCLOMYCIN DERIVATIVES, COMPOSITIONS THEREOF AND PROCESS OF USE THEREOF

[75] Inventors: Beat Müller, Reinach; Wilhelm Kump, Biel-Benken; Oskar Wacker, Basel, all of Switzerland

[73] Assignee: Ciba-Geigy Corporation, Ardsley, N.Y.

[21] Appl. No.: 1,996

[22] Filed: Jan. 8, 1979

Related U.S. Application Data

[63] Continuation of Ser. No. 796,286, May 12, 1977, abandoned.

[30] Foreign Application Priority Data

May 21, 1976 [CH] Switzerland ............ 6445/76

[51] Int. Cl.³ ............ A61K 31/495; C07D 498/08
[52] U.S. Cl. ............... 424/250; 260/239.3 B
[58] Field of Search ............ 260/239.3 B; 424/250

[56] References Cited

U.S. PATENT DOCUMENTS 3,873,526  3/1975  Kamiya et al. ............ 260/239.3 B
3,923,790 12/1975  Imanaka et al.
4,145,344  3/1979  Muller et al. ............ 260/239.3 B
4,215,043  7/1980  Kamiya et al. ............ 260/239.3 B

FOREIGN PATENT DOCUMENTS 1464962  2/1977  United Kingdom ........ 260/239.3 B

Primary Examiner—Robert T. Bond
Attorney, Agent, or Firm—Prabodh I. Almaula

[57] ABSTRACT

Derivatives of 5-norbicyclomycin of the formula

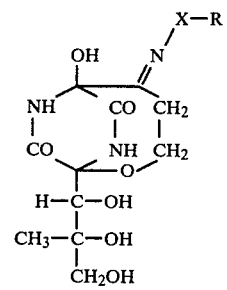

wherein R represents an unsubstituted or substituted monovalent hydrocarbon radical in which one, two or more carbon atoms can be replaced by heteroatoms, and X represents a bivalent group of the formula —O— or —N(R')—, wherein R' has one of the meanings assigned to R, whilst R and R', if both have a meaning which is different from hydrogen, can also be linked to each other through a C—C bond or an oxygen, sulphur or nitrogen atom, and corresponding compounds, in which at least one hydroxyl group is protected, and salts of said compounds, provided they contain salt-forming groups, are useful as antibiotics, especially against Enterobacteriaceae, or as intermediates for the production of such antibiotics. They are obtained by condensing a corresponding 5-norbicyclomycin-5-one with a compound of the formula R—X—NH₂ in which X and R have the above meaning.

9 Claims, No Drawings

BICYCLOMYCIN DERIVATIVES, COMPOSITIONS THEREOF AND PROCESS OF USE THEREOF

This is a Continuation of application Ser. No. 796,286 filed on May 12, 1977, now abandoned.

The present invention relates to bicyclic compounds having the basic skeleton of the 2-oxa-7,9-diazabicyclo[4,2,2]decane of the formula

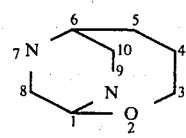

and, in particular, derivatives of the 5-norbicyclomycin of the formula

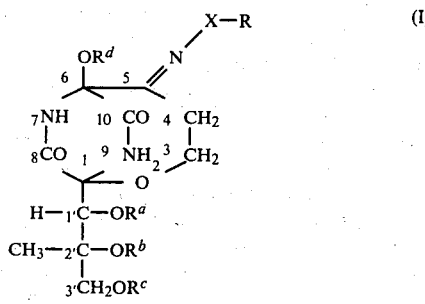

wherein each of $R^a$, $R^b$, $R^c$ and $R^d$ individually represents a hydrogen atom or a hydroxyl protective group $R^1$, or any two of the symbols $R^a$, $R^b$ and $R^c$ together represent a bivalent hydroxyl protective group $R^2$, or these three symbols together represents a trivalent hydroxyl protective group $R^3$, R represents an unsubstituted or substituted monovalent hydrocarbon radical in which one, two, or more carbon atoms can be replaced by heteroatoms, or represents an acyl radical Ac or a hydrogen atom, and X represents a bivalent group of the formula —O— or —N(R')—, wherein R' has one of the meanings assigned to R, and R and R', if both have a meaning which is different from hydrogen, can also be linked to each other through a C—C bond or an oxygen, sulphur or nitrogen atom, and to salts of these compounds, provided they contain salt-forming groups, and also to a process for the manufacture of said compounds and to preparations which contain them and to the use of the latter, as well as to therapeutic methods of combating infectious diseases which comprise the use of these compounds and preparations.

In the above compounds of the formula I, the group —X—R is syn- or anti-oriented with respect to the rest of the molecule, for example in relation to the 6-hydroxyl group. Unless otherwise specifically stated, a process product can be both a mixture of both isomeric forms and an individual isomer.

A hydroxyl protective group $R^1$ is a group which can be replaced by hydrogen, chiefly a monovalent acyl group $Ac^1$, also a triarylmethyl group, in particular the trityl group, a 2-oxaalkyl or 2-oxacycloalkyl group, in particular a 1-butoxyethyl or 2-tetrahydropyranyl group, as well as an organic silyl group.

A bivalent hydroxyl protective group $R^2$ formed by any two of the symbols $R^a$, $R^b$ and $R^c$ can be the bivalent acyl group $Ac^2$ of an organic dicarboxylic acid, preferably one containing not more than 18 carbon atoms; such a group is preferably the oxalyl group. It can also be a carbonyl, thiocarbonyl, sulphonyl or sulphinyl group, but is primarily an acylic, carbocyclic or carbocyclic-acyclic ylidene radical, preferably one having not more than 18 carbon atoms, which can be substituted in the 1-position by one or two alkoxy groups, preferably lower alkoxy groups.

A hydroxyl protective group $R^3$ formed by all three symbols $R^a$, $R^b$ and $R^c$ is in particular an acyclic ylidyne radical, chiefly a lower alkylidyne radical, for example the ethylidyne radical and preferably the methylidyne radical, which can also carry carbocyclic or heterocyclic groups.

Unless stated to the contrary, the term "lower" used throughout this specification to qualify organic groups and radicals means that these contain not more than 7, preferably not more than 4, carbon atoms.

A hydrocarbon radical is an acyclic, carbocyclic or carbocyclicacyclic hydrocarbon radical which contains preferably not more than 18 carbon atoms. A hydrocarbon radical in which one, two, or more carbon atoms are replaced by heteroatoms is in particular a heterocyclic or heterocyclic-acyclic radical. Preferred heteroatoms are oxygen, sulphur and nitrogen atoms, and also phosphorus and silicon. All these radicals can be unsubstituted or substituted and contain one, two, or more multiple bonds, such as double and triple bonds. Cyclic radicals, wherein at least one 6-membered carbocyclic ring or a 5- to 8-membered heterocyclic ring is completely unsaturated (i.e. containing the maximum number of non-cumulated double bonds) are designated as aromatic radicals. Carbocyclic radicals in which at least one ring is a 6-membered aromatic ring (i.e. the benzene ring) are designated as aryl radicals.

A monovalent acyclic hydrocarbon radical is in particular a linear or branched lower alkyl, lower alkenyl, lower alkadienyl or lower alkynyl radical. An acyclic ylidene radical is an analogous radical in which two free valencies originate from a single carbon atom and is in particular a lower alkylidene and lower alkenylidene radical.

Examples of lower alkyl radicals are methyl, ethyl, n-propyl, isopropyl, n-butyl, isobutyl, sec.-butyl or tert.-butyl, as well as n-pentyl, isopentyl, n-hexyl, isohexyl or n-heptyl. Examples of lower alkenyl radicals are: vinyl, allyl, propenyl, isopropenyl, 2- or 3-methallyl and 2- or 3-butenyl. Lower alkynyl is for example propargyl or 2butynyl. Examples of lower alkylidene radicals are methylene, isopropylidene or isobutylidene, and a lower alkenylidene radical is for example vinylidene.

A monovalent carbocyclic hydrocarbon radical is in particular a mono-, bi- or polycyclic cycloalkyl, cycloalkenyl or cycloalkadienyl radical, or a corresponding aryl radical which contains aromatic rings. Radicals containing not more than 12 ring carbon atoms and 3- to 8-membered, preferably 5- and/or 6-membered, rings, are preferred. Such radicals can also carry one or more acyclic radicals, for example those referred to above, and in particular the lower alkyl radicals, or further carbocyclic radicals. A carbocyclic ylidene radical is a carbocyclic radical in which two free valencies originate from a single carbon atom, and is in particular a monocyclic cycloalkylidene radical or an unsaturated analogue thereof. Carbocyclic-acyclic radicals are hydrocarbon radicals in which an acyclic monovalent radical or an acyclic ylidene radical, in particular one containing not more than 7, preferably not more than 4, carbon atoms, carries one or more carbocyclic, optionally aromatic, radicals as defined above. Cycloalkyl-lower alkyl or aryl-lower alkyl and cycloalkyl-lower alkylidene or aryl-lower alkylidene radicals, as well as their analogues which are unsaturated in the ring and/or in the side-chain are to be particularly mentioned.

Examples of cycloalkyl radicals are cyclopropyl, cyclobutyl, cyclopentyl, cyclohexyl, cycloheptyl and cyclooctyl, as well as bicyclo[2,2,2]octyl, 2-bicyclo[2,2,1]heptyl and adamantyl, and also 1-, 2- or 3-methylcyclopentyl, 4tert.-butylcyclohexyl, 4,4-dimethylcyclohexyl, 2,4,6-trimethylcyclohexyl and 2,4,4,6-tetramethylcyclohexyl. A cycloalkenyl radical is for example one of the cycloalkyl groups already mentioned which carries a double bond in the 1, 2- or 3-position, such as 1-, 2- or 3-cyclopentenyl and 1-, 2- or 3-cyclohexenyl. A cycloalkadienyl radical is for example 1,4-cyclohexadienyl. Examples of cycloalkylidene groups are cyclopentylidene and cyclohexylidene radicals, and among their unsaturated analogues cyclopentadienylidene is to be particularly mentioned. Examples of cycloalkyllower alkyl or lower alkenyl radicals are cyclopropyl-, cyclopentyl-, cyclohexyl- or cycloheptyl-methyl -1- or -2-ethyl-, -1-or -2-vinyl, -1-, -2- or -3-propyl or -allyl, and also dicyclohexylmethyl and tricyclohexylmethyl. Examples of cycloalkenyllower alkyl or lower alkenyl radicals are 1-, 2- or 3-cyclopentenyl- or 1-, 2- or 3-cyclohexenyl-methyl, -1- or -2-ethyl, -1- or -2-vinyl, -1-, -2- or -3-propyl or -allyl. A cycloalkyl-lower alkylidene radical is for example cyclohexylmethylene or dicyclohexylmethylene, and a cycloalkenyl-lower alkylidene radical is for example 3-cyclohexenylmethylene.

An aryl radical is in particular a phenyl radical, and also a naphthyl radical, such as 1- or 2-naphthyl, a biphenylyl radical, as in particular 4-biphenylyl, as well as an anthryl, fluorenyl and azulenyl radical. Preferred aryl-lower alkyl, aryl-lower alkenyl and aryl-lower alkylidene radicals are for example phenyl-lower alkyl or phenyl-lower alkenyl radicals, for example benzyl, 1- or 2-phenylethyl, 1-, 2- or 3-phenylpropyl, diphenylmethyl (viz. benzhydryl), trityl and 1- or 2-naphthylmethyl radicals, and styryl or cinnamyl radicals respectively, and benzylidene.

Heterocyclic radicals, including the heterocyclic-acyclic radical and the acyl radicals of heterocyclic or heterocyclicacyclic carboxylic acids, are in particular monocyclic, but also bi- or polycyclic aza-, thia-, oxa-, thiaza-, thiadiaza-, oxaza-, diaza-, triaza- or tetraazacyclic radicals of aromatic character, and corresponding partially or completely saturated heterocyclic radicals of this kind. Such radicals can carry further acyclic, carbocyclic or heterocyclic radicals, for example the above carbocyclic or aryl radicals and can be mono-, di-, or polysubstituted. The acyclic portion of heterocyclicacyclic radicals has the meaning as that for example of the corresponding portion of the carbocyclic-acyclic radicals. They are preferably unsubstituted or substituted monocyclic, monoaza-, monothia- or monooxocyclic radicals, such as aziridinyl, oxiranyl and thiiranyl radicals, and in particular heterocyclic radicals of aromatic character, such as pyridyl, for example 2-pyrryl or 3-pyrryl, pyridyl, for example 2-, 3- or 4-pyridyl and pyridinio, and thienyl, for example 2- or 3-thienyl, or furyl, for example 2-furyl; bicyclic monoaza-, monooxa- or monothiacyclic radicals, such as indolyl, for example 2- or 3-indolyl, quinolinyl, for example 2- or 4-quinolinyl, isoquinolinyl, for example 1-isoquinolinyl, benzofuranyl, for example 2- or 3-benzofuranyl, or benzothienyl, for example 2- or 3-benzothienyl; monocyclic diaza-, triaza-, tetraaza, oxaaza-, thiaza- or thiadiazacyclic radicals, such as imidazolyl, for example 2-imidazolyl, pyrimidinyl, for example 2- or 4-pyrimidinyl, triazolyl, for example 1,2,4-triazol-3-yl, tetrazolyl, for example 1- or 5-tetrazolyl, oxazolyl, for example 2-oxazolyl, isoxazolyl, for example 3- or 4-isoxazolyl, thiazolyl, for example 2-thiazolyl, isothiazolyl, for example 3- or 4-isothiazolyl or 1,2,4- or 1,3,4-thiadiazolyl, for example 1,2,4-thiadiazol-3-yl or 1,3,4-thiadiazol-2-yl; or bicyclic diaza-, oxaza or thiazacyclic radicals, such as benzimidazolyl, for example 2-benzimidazolyl, benzoxazolyl, for example 2-benzoxazolyl, or benzthiazolyl, for example 2-benzthiazolyl. Corresponding partially or completely saturated radicals are for example tetrahydrothienyl, such as 2-tetrahydrothienyl, tetrahydrofuryl, such as 2-tetrahydrofuryl, pyrrolidyl, such as 2-pyrrolidyl, pyrrolidino (i.e. N-pyrrolidyl) and 2,3,4,5-tetramethylpyrrolidino, tetrahydropyridyl, such as $\Delta^1$-, $\Delta^2$- or $\Delta^3$-piperideino or -piperideinyl, or piperidyl, such as piperidino, 2-, 3- or 4-piperidyl, and also morpholino, thiomorpholino, piperazino and N'-lower alkylpiperazino, in particular N'-methylpiperazino. These radicals can also carry one or more acyclic, carbocyclic or heterocyclic radicals, in particular those mentioned above. Heterocyclic-acyclic radicals are derived in particular from acyclic radicals having not more than 7, preferably not more than 4, carbon atoms, for example from those mentioned above, and can carry two or more heterocyclic radicals, for example those mentioned above.

The hydrocarbon radicals, including heterocyclic radicals, can be substituted by one, two, or more alike or different substituents. Suitable substituents are: free, etherified and esterified hydroxyl groups; mercapto, lower alkylthio and substituted or unsubstituted phenylthio groups; halogen atoms, such as chlorine and fluorine but also bromine and iodine atoms; azido, oxo and nitro groups; primary, secondary and tertiary amino groups; acylamino groups corresponding to the secondary and tertiary amino groups, and diacylamino groups; sulphamino groups which can be in salt form, for example in the form of alkali metal salts; carboxyl groups which can be functionally modified, such as carboxyl groups in salt from or esterified carboxyl groups; carbamoyl, ureidocarbonyl or guanidinocarbonyl groups which can carry one or two hydrocarbon radicals, and cyano groups; and sulpho groups which can be functionally modified, such as sulphamoyl groups or sulpho groups in salt form.

An etherified hydroxyl group is for example a lower alkoxy group, such as the methoxy, ethoxy, propoxy, isopropoxy, butoxy and tert.-butoxy group, which can also be substituted. Thus such a lower alkoxy group can be substituted by halogen atoms, in particular in the 2-position, for example in the 2,2,2-trichloroethoxy, 2-chloroethoxy or 2-iodoethoxy moiety, or by lower alkoxy groups, especially in the 1-position, as in the butoxyethoxy moiety, or in the 2-position, as in the 2-methoxyethoxy moiety. In addition, etherified hydroxyl groups are also substituted or unsubstituted phenoxy and phenyl-lower alkoxy groups, in particular benzyloxy, benzhydryloxy and triphenylmethoxy (trityloxy) groups, and heterocyclyloxy groups, as in particular 2-tetrahydrofuranyloxy and 2-tetrahydropxranyloxy groups. Etherified hydroxyl groups are also to be understood as meaning silylated hydroxyl groups, for example those which occur in tri-lower alkylsilyloxy groups, such as trimethylsilyloxy or dimethyl-tert.-butylsilyloxy groups, or phenyl-dilower alkylsilyloxy or lower alkyl-diphenylsilyloxy groups.

An esterified hydroxyl group can be derived both from an inorganic and an organic acid. Examples of the corresponding inorganic acids are sulphuric and phosphoric acids, and, in particular, hydrohalic acids, such as hydrofluoric, hydrochloric, hydrobromic and hydriodic acid. In a hydroxyl group esterified with an organic acid, the hydrogen atom of the hydroxyl group is replaced by the acyl group Ac. An esterified hydroxyl group can also be a lactonised hydroxyl group.

The acyl group Ac is derived from an organic acid and has one of the meanings assigned to the symbol $Ac^1$ hereinafter or represents the molovalent radical of an acyclic, carbocyclic or heterocyclic sulphonic acid, preferably one having not more than 18 carbon atoms, for example in particular an optionally halogenated lower alkanesulphonyl group, such as the methanesulphonyl and trifluoromethanesulphonyl group, a substituted or unsubstituted cycloalkanesulphonyl group, such as a camphor10-sulphonyl group, or a benzenesulphonyl group which is unsubstituted or substituted by halogen, nitro, lower alkoxy and/or lower alkyl, such as the benzenesulphonyl, p-toluenesulphonyl (i.e. tosyl), p-chlorobenzenesulphonyl, p-bromobenzenesulphonyl and 2,4-dinitrobenzenesulphonyl group.

The acyl group $Ac^1$ is the monovalent radical derived from a hemiderivative of carbonic acid, from a carboxylic acid or from formic acid, i.e. the formyl group, and an analogous radical which contains sulphur instead of oxygen. The acyl radical of a hemiderivative of carbonic acid is in particular the acyl radical of a corresponding hemiester, for example preferably a lower alkoxycarbonyl or aryl-lower alkoxycarbonyl group which is unsubstituted or substituted in particular by lower alkyl, lower alkoxy, nitro and/or halogen, such as methoxycarbonyl, ethoxycarbonyl, tert.-butoxycarbonyl, 2,2,2-trichloroethoxycarbonyl, 2-iodoethoxycarbonyl, benzyloxycarbonyl, 2-phenyl-2-propoxycarbonyl, 2-p-tolyl-2-propoxycarbonyl, 2-p-biphenylyl-2-propoxycarbonyl, 1,1-diphenylethoxycarbonyl or p,p'-dimethoxybenzhydryloxycarbonyl group. Acyl radicals of the following derivatives of carbonic acid are also to be mentioned: a carbamoyl, carbazoyl, unreidocarbonyl or guanidino group, in which the nitrogen atoms can be partly or completely substituted by hydrocarbon radicals, as well as corresponding thio analogues, as in particular a thiocarbamoyl or thiocarbazoyl group which is unsubstituted or substituted by one or two hydrocarbon radicals. The acyl radical of a carboxylic acid is a radical in which one of the above defined substituted or unsubstituted acyclic, carbocyclic, carbocyclic-acyclic, heterocyclic and heterocyclic-acyclic radicals is bonded to the carbonyl group. Acyl radicals of the following monocarboxylic acids having not more than 18 carbon atoms are particularly preferred: acyclic carboxylic acids, in particular lower alkanecarboxylic acids, such as propionic, butyric, isobutyric, valeric, isovaleric, capronic, trimethylacetic, enanthic and diethylacetic acid, and, most preferably, acetic acid, but also corresponding halogenated lower alkanecarboxylic acids, such as chloroacetic acid, bromoacetic acid or α-bromoisovaleric acid; carbocyclic or carbocyclic-acyclic monocarboxylic acids, for example cyclopropane-, cyclobutane-, cyclopentane- and cyclohexanecarboxylic acid and cyclopropyl-, cyclobutyl-, cyclopentyl- or cyclohexylacetic acid or cyclopentyl- or cyclohexylpropionic acid; aromatic carbocyclic carboxylic acids, for example benzoic acids which are unsubstituted or substituted by halogen, such as fluorine, chlorine or bromine atoms, and/or by hydroxyl, lower alkoxy, lower alkyl and nitro groups; aryl- or aryloxy-lower alkanecarboxylic acids and the analogues thereof which are unsaturated in the chain, for example phenylacetic or phenoxyacetic acids which are unsubstituted or substituted by the same substituents as indicated above for benzoic acid, phenylpropionic acids and cinnamic acids; and also heterocyclic acids, for example furane-2-carboxylic acid, 5-tert.-butylfurane-2-carboxylic acid, 5-bromofurane-2-carboxylic acid, thiophene-2-carboxylic acid, nicotinic or isonicotinic acid, 3-(4-pyridyl)-propionic acid, and pyrrol-2- or -3-carboxylic acids which can be substituted by lower alkyl groups, and corresponding α-aminoacids, in particular α-amino-lower alkanecarboxylic acids, for example glycine, phenylglycine, proline, leucine, valine, tyrosine, histidine and asparagine.

A bivalent acyl radical $Ac^2$ is derived chiefly from a dicarboxylic acid having not more than 18 carbon atoms which in turn is derived from the above optionally substituted acyclic, carbocyclic, carbocyclic-acyclic, heterocyclic and heterocyclic-acyclic radicals in that it carries two carboxyl groups, optionally also at the heteroatoms. Examples of such dicarboxylic acids are: oxalic acid, malonic acid, mono- or di-lower alkylmalonic acid, succinic acid, glutaric acid, adipic acid, maleic acid, itaconic acid, citraconic acid, angelic acid, 1,1-cyclopentane- or 1,1-cyclohexane-dicarboxylic acid, a phthalic, quinolic or phenylsuccinic acid which is unsubstituted or substituted by halogen atoms, such as fluorine, chlorine or bromine, atoms, and/or lower alkyl, lower alkoxy and nitro groups, and also tartronic acid, mesoxalic acid, oxalacetic acid, malic acid, tartaric acid, a tartaric acid which is esterified or etherified at the hydroxyl groups, glutamic acid and aspartic acid and derivatives of these last two acids with protected amino groups. $Ac^2$ can also be a divalent radical of ortho-carbonic acid or of an ortho-carboxylic acid, in particular a di-lower alkoxymethylene group, or a 1-lower alkoxyalkylidene or α-lower alkoxybenzylidene group, for example methoxymethylene, 1-methoxyethylidene, ethoxymethylene, 1-ethoxyethylidene, α-methoxybenzylidene and α-ethoxybenzylidene group.

An esterified carboxyl group is one in which the hydrogen atom is replaced by one of the hydrocarbon radicals referred to above, preferably a lower alkyl or phenyl-lower alkyl radical. An esterified carboxyl group is for example the methoxy-, ethoxy-, tert.-butoxy- or benzyloxycarbonyl group, and also a lactonised carboxyl group.

A primary amino group is a group of the formula —NH₂. An acylamino group corresponding to this group has the formula —NH—Ac, wherein Ac is as defined above, and a corresponding diacylamino group carries two monovalent acyl groups Ac which can be the same or different, or a bivalent acyl group $Ac^2$. A secondary amino group carries in place of one of both hydrogen atoms a monovalent hydrocarbon radical in which one or more carbon atoms can be replaced by heteroatoms, for example one of the above radicals. An acylamino group derived therefrom carries in addition the monovalent acyl group Ac defined above. A tertiary amino group carries two such monovalent hydrocarbon radicals (including the analogous heterocyclic radicals), which can be alike or different. If the amino group carries two substituents of the same or different kind (i.e. hydrocarbon radicals and/or acyl radicals), these substituents can be linked to each other through a C—C bond or by an oxygen, sulphur or substituted or unsubstituted nitrogen atom, and together with the nitrogen atom of the amino group can form a nitrogen-containing heterocyclic ring. Examples of especially preferred amino and acylamino groups are: lower alkylamino or di-lower alkylamino, such as methylamino, ethylamino, dimethylamino or diethylamino groups, and pyrrolidino, piperidino, morpholino, thiomorpholino and piperazino or 4-methylpiperazino groups, phenylamino, diphenylamino and benzylamino, which are unsubstituted or substituted by lower alkyl, lower alkoxy groups, halogen atoms and/or nitro groups. Acylamino is in particular carbamoylamino, carbazoylamino, mono- and di-lower alkylcarbamoylamino, such as mono- and dimethylcarbamoylamino, lower alkoxycarbonylamino, for example methoxycarbonylamino, ethoxycarbonylamino or tert.-butyloxycarbonylamino, halogen-lower alkoxycarbonylamino, such as 2,2,2-trichloroethoxycarbonylamino, phenyl-lower alkoxycarbonylamino, such as 4-methoxybenzyloxycarbonylamino, lower alkanoylamino, such as formylamino, acetylamino or propionylamino, and succinimido, glutarimido and phthalimido, and also 2-oxopyrrolidino, 2-oxopiperidino and 2-oxoperhydroazepino, which are derived from γ-butyro-, δ-valero and ε-caprolactam, as well as benzenesulphonylamino groups which are unsubstituted or substituted by halogen atoms, such as fluorine, chlorine and bromine atoms, and/or lower alkyl, lower alkoxy and nitro groups, such as the benzenesulphonylamino, p-toluenesulphonylamino (tosylamino) and p-bromobenzenesulphonylamino group. The above definition also relates to amino groups which are a constituent of other functional groups, such as carbamoyl, carbazoyl, ureido, guanidino, hydrazino, semicarbazido, semicarbazono or sulphamoyl groups.

The compounds of the formula I, provided they contain salt-forming groups, can be in the form of salts, preferably physiologically tolerable salts. If a compound of the formula I contains an acid group, such as carboxyl or sulpho, salts can be formed with bases, viz. primarily metal or ammonium salts, for example sodium, potassium, magnesium or calcium salts, or ammonium salts with ammonia or suitable organic amines. Suitable amines for the salt formation are in particular acyclic, carbocyclic and carbocyclic-acyclic primary, secondary and, most preferably, tertiary amines, di- or polyamines, and heterocyclic bases, such as lower alkylamines, for example triethylamine, hydroxy-lower alkylamines, for example 2-hydroxyethylamine, di-(2-hydroxyethyl)-amine or tri-(2-hydroxyethyl)-amine or tri-(2-hydroxyethyl)-amine, basic aliphatic esters of carboxylic acids, for example 2-(diethylamino)-ethyl 4-aminobenzoate, lower alkylenamines, for example 1-ethylpiperidine, cycloalkylamines, for example dicyclohexylamine, or benzylamines, for example N,N'-dibenzylethylenediamine, and bases of the pyridine type, for example pyridine, collidine or quinoline. Compounds of the formula I, which contain a basic group in the substituents, can form addition salts, in particular acid addition salts, for example with inorganic acids, such as hydrochloric acid, sulphuric acid or phosphoric acid, or with suitable organic carboxylic or sulphonic acids, for example trifluoroacetic acid. Compounds of the formula I which contain both an acid and a basic group as substituents, can also be in the form of an inner salt, i.e. in zwitterion form. Addition salts also comprise quaternary salts which are formed, for example, by addition of a hydrocarbon halide to a tertiary amino group or the aromatic nitrogen atom of an aromatic heterocyclic ring. Examples are the methanesulphonate, the bromide or the chloride of a tri-lower alkylammonio compound, such as a trimethylammonio, pyridinio, pyrimidinio, quinolinio or isoquinolinio compound.

The novel compounds of the present invention exhibit useful pharmacological, especially antibiotic, for example antibacterial, properties, and/or can be used as intermediates for obtaining such compounds.

Particularly preferred compounds are those of the formula

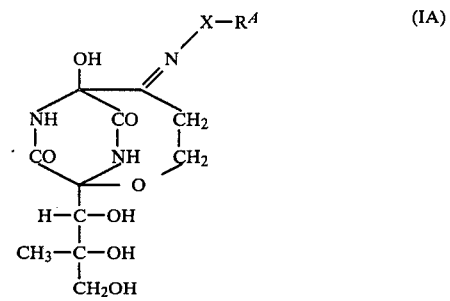

wherein $R^4$ represents a hydrogen atom, an optionally modified lower alkyl radical alk, a substituted or unsubstituted phenyl radical Ph or an acyl group $Ac^4$, and X represents a group of the formula —NH— or preferably —O—, and salts of these compounds, provided they contain salt-forming groups.

The lower alkyl radical alk is in particular one of the unsubstituted lower alkyl radicals referred to above, preferably a linear lower alkyl radical which can also be modified, i.e. which can carry one or more monocyclic aryl and/or heterocyclyl radicals which are unsubstituted or substituted, for example as indicated hereinafter, and/or which can be substituted by one or more functional groups. Potential functional groups are in particular hydroxyl groups, lower alkoxy groups, such as methoxy and ethoxy groups, lower alkanoyloxy groups, such as formyloxy and acetoxy groups, amino groups which can be mono- or disubstituted by lower alkyl, such as methylamino, dimethylamino, diethylamino and propylamino, carboxyl carbamoyl and lower alkoxycarbonyl groups, such as methoxycarbonyl and ethoxycarbonyl groups. Examples of such modified radicals alk are benzyl and furfuryl radicals, which can also be substituted in the manner indicated hereinafter, and also free or esterified carboxy-lower alkyl radicals, such as carboxymethyl, methoxycarbonylmethyl and ethoxycarbonylmethyl radicals, ω-amino-ω-carboxy-lower alkyl radicals, such as 2-amino-2-carboxyethyl, 2-methylamino-2-carboxyethyl or 3-carboxypropyl radicals, and the analogues thereof with esterified carboxyl group, amino-lower alkyl radicals, such as 2-aminoethyl, 2-dimethylaminoethyl, 3-aminopropyl or 4-aminobutyl radicals, and hydroxy-lower alkyl radicals, such as the hydroxymethyl, 2-hydroxyethyl, 2-hydroxypropyl, acetoxymethyl, 2-formyloxyethyl and 2-acetoxyethyl radical, and lower alkoxy-lower alkyl radicals, such as the methoxymethyl, ethoxymethyl, 2-methoxyethyl and 2-ethoxyethyl radical. The monocyclic aryl and heterocyclyl radicals which are also preferably present in the subsequently defined acyl group $Ac^A$, are in particular phenyl, furyl, thienyl, pyridyl, pyrimidyl, oxazolyl, imidazolyl and tetrazolyl radicals which can be substituted by one or more halogen atoms, such as fluorine, chlorine and bromine atoms, nitro groups, lower alkyl radicals, such as methyl radicals, hydroxyl groups, lower alkoxy groups, such as methoxy and ethoxy groups, methylenedioxy groups, amino groups, di-lower alkylamino groups, such as dimethylamino and diethylamino groups, alkanoylamino groups, such as acetamino groups, and/or carboxyl groups. In analogous manner, the phenyl radicals represented by the symbol Ph can also be substituted.

The monovalent acyl group $Ac^A$ is the radical of a lower alkanesulphonic acid, for example the methanesulphonyl group, or of a benzenesulphonic acid which is unsubstituted or substituted as indicated above, for example the benzenesulphonyl, p-toluenesulphonyl (tosyl), p-bromobenzenesulphonyl and p-nitrobenzenesulphonyl group, and also the radical of a hemiderivative of carbonic acid or thiocarbonic acid, for example the methoxycarbonyl, ethoxycarbonyl, tert.-butoxycarbonyl or benzyloxycarbonyl group, and also the carbamoyl and thiocarbamoyl group, in addition the acyl radical of a modified or unmodified lower alkanecarboxylic acid or of a substituted or unsubstituted monocyclic aryl or heterocyclic carboxylic acid, and also the formyl group. The modified or unmodified lower alkanecarboxylic acids correspond to the above defined lower alkyl radicals which can carry aryl and/or heterocyclyl radicals and/or be substituted by functional groups. Preferred substituents of these acyl groups are in particular primary amino groups, tertiary amino groups, for example dimethylamino, diethylamino as well as piperidino, morpholino and N-methylpiperazino groups, and ammonio salts derived therefrom, including the quaternary salts, and, in addition, carboxyl groups which can be in the free form, as salts or as lower alkyl esters, in particular methyl and ethyl esters. Examples of such lower alkanecarboxylic acid acyl groups are in particular: acetyl, propionyl, butyryl, methoxalyl, glycyl, N,N-dimethylglycyl, α- and γ-glutamyl, phenylacetyl, furylacetyl, pyridinioacetyl (e.g. as chloride), and trimethylammonioacetyl (e.g. as chloride), and succinamoyl. The substituted or unsubstituted monocyclic aryl- or heterocyclylcarboxylic acid acyl groups correspond to the above defined aryl and heterocyclyl radicals. Examples of such acyl groups are in particular: benzoyl, p-nitrobenzoyl, p-methoxybenzoyl, p-chlorobenzoyl, δ-, m- and p-toluoyl, 2,4,6-trimethylbenzoyl, furoyl, thenoyl, 2-pyridinecarbonyl, nicotinoyl, isonicotinoyl, and 1- and 5-tetrazolcarbonyl.

The novel compounds reveal useful pharmacological properties, as is shown both in the in vitro test and in animal tests. Thus the in vitro test results show them to have antibiotic, in particular antibacterial, properties, for example against Enterobacteria (in concentrations of approx. 0.025 to approx. 0.5 mg/ml). In animal tests too, or against Proteus sp. (in concentrations of approx. 0.1 to approx. 0.5 mg/ml), for example on mice in doses of approx. 16 to approx. 100 mg/kg (subcutaneous administration) the novel compounds show antibacterial properties against Escherichia coli and Klebsiella, and, in doses of approx. 20 to approx. 700 mg/kg (subcutaneous administration), against Proteus sp. To be singled out for special mention is 5-methoxyimino-5-norbicyclomycin, i.e. the compound of the formula IA, wherein $-X-R^A$ represents the methoxy group, for which an effective does $ED_{50}$ of approx. 16 to 20 mg/kg was found against Enterobacteria, for example Escherichia coli and Proteus sp., when administered subcutaneously to mice. Bicyclomycin, to the contrary, is not sufficiently effective against Proteus. The novel compounds can therefore be used for example in the form of antibiotic preparations for the treatment of infectious diseases, or as preservatives, or as additives to animal feeds. In addition, they can be used for the preparation of other compounds with such an antibiotic action.

The compounds of the formula I are obtained by reacting a 5-norbicyclomycin-5-one compound of the formula II

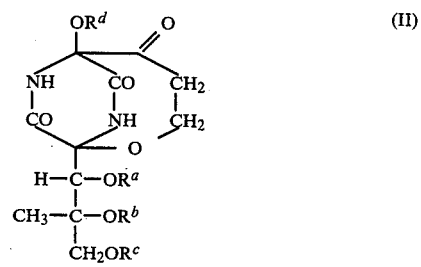

wherein $R^a$, $R^b$, $R^c$ and $R^d$ are as defined in formula (I), with a compound of the formula $$R-X-NH_2 \qquad (III)$$

wherein R and X are as already defined, or with a salt thereof, and, if desired, in a resultant compound, removing or introducing one or more hydroxyl protective groups $R^a$, $R^b$, $R^c$ and/or $R^d$ or converting them into other hydroxyl protective groups, and, if desired, within the definition of the final products, converting a resultant compound into another compound, and/or, if desired, converting a resultant compound with a salt forming group into the free compound or into another salt, and/or, if desired, separating individual isomers from a resultant isomer mixture.

Preferably, 5-norbicyclomycin-5-one, which has free hydroxyl groups, is used as starting material of the formula II.

Starting materials of the formula III are hydroxylamine and O-substituted hydroxylamines of the formula $$R-O-NH_2 \qquad (IIIa)$$

wherein R is as defined above and in particular has the meaning assigned to the symbol $R^A$, and the corresponding acid addition salts. Starting materials of the formula III are also hydrazine or hydrazine hydrate, 1,1-disubstituted hydrazines and, in particular monosubstituted hydrazines, including semicarbazide and thiosemicarbazide, and the corresponding salts. They are characterised by the formula

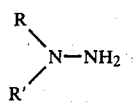

(IIIb)

wherein R and R' are as already defined herein, whilst both radicals, if they are different from hydrogen, can also be linked to each other through a C-C bond or by an oxygen, sulphur or nitrogen atom. Preferably, however, R has one of the meanings assigned to the symbol $R^A$, whilst R' at the same time represents a hydrogen atom. Salts of compounds of the formula III are primarily acid addition salts, in particular with mineral acids, such as hydrohalic acids, for example hydrochloric or hydrobromic acid, or sulphuric acid.

The above reaction is carried out in a manner known per se, and, when using acid addition salts of compounds of the formula III, in the presence of a basic reagent. Suitable bases are inorganic bases, such as carbonates or hydrogen carbonates of alkali metals or alkaline earth metals, for example sodium hydrogen carbonate, or organic bases, for example tertiary organic bases, such as corresponding heterocyclic bases, for example pyridine or quinoline, or tertiary aliphatic, cycloaliphatic or aromatic amines, for example tri-lower alkylamines, such as triethylamine, and also alkali metal or alkaline earth metal salts of organic carboxylic acids, such as lower alkanecarboxylic acids, for example acetic acid, such as sodium acetate.

The reaction is preferably carried out in the presence of a suitable solvent or diluent, such as an alcohol, for example a lower alkanol, such as methanol or ethanol, an ether, such as a cyclic ether, for example tetrahydrofurane or dioxane, or an ether of a glycol, such as a lower alkyl ether of a glycol or polyglycol, for example ethylene glycol dimethyl ether or diethylene glycol dimethyl ether, or a halogenated hydrocarbon, such as a chlorinated alkane, for example methylene chloride, and water, or a solvent or diluent mixture, with cooling or preferably with heating, for example at temperatures of approx. 20° to approx. 100° C., and, if appropriate, in a closed reaction vessel and/or in an inert gas atmosphere, for example in a nitrogen or argon atmosphere.

In the process of the present invention and also in any additional steps which it may be necessary to carry out, free functional groups which are present in the starting materials or in the compounds obtained in accordance with the process and which do not participate in the reaction, for example free amino groups in the group R, can, if necessary, be temporarily protected by acylation, tritylation or silylation, and, in particular, free hydroxyl groups in the bicyclomycin skeleton, for example by etherification or esterification, preferably with the protective groups represented by $R^1$, $R^2$ and $R^3$, in a manner known per se, and, when the reaction is complete, set free, if desired, individually or together. Thus, for example, hydroxyl groups which are protected as tetrahydropyranyl ether, for example in the 1'-, 3'- and/or 6-position, can be set free by conventional acid catalysed hydrolysis.

Resultant compounds of the formula I can be converted in a manner known per se into other compounds of the formula I.

For example, in a compound of the formula I, in which R and R' in the grouping —N(R')-R represent hydrogen, and each of $R^a$, $R^b$ and $R^c$ is preferably different from hydrogen, the amino group can be substituted by methods which are known per se, in particular acylated, in a manner known per se, by treatment with acids, such as carboxylic acids, or reactive derivatives thereof, such as anhydrides, halides, for example chlorides, and ketenes.

It is also possible, for example in a compound of the formula I, wherein R in the grouping —O-R represents hydrogen, to substitute, preferably to alkylate, the free hydroxyl group by methods which are known per se. In particular, a corresponding oxime with a free hydroxyl group can be treated in a manner known per se with a diazoalkane, preferably diazomethane, preferably avoiding a large excess of the reactant and inappropriately long reaction times.

Salts of compounds of the formula I can be prepared in a manner known per se. Thus salts of compounds of the formula I with an acid grouping can be formed for example by treatment with metal compounds, such as hydroxides, carbonates and hydrocarbonates of alkali metals or alkaline earth metals, and also with alkali metal salts of suitable carboxylic acids, for example the sodium salt of α-ethylcaproic acid, or with ammonia or a suitable organic amine, preferably using stoichiometric amounts or only a small excess of the salt-forming agent. Acid addition salts of compounds of the formula I with basic groups are obtained in similar manner, for example by treatment with an acid or a suitable anion exchanger. Inner salts of compounds of the formula I which contain a salt-forming amino group and a free carboxyl group, can be formed for example by neutralising salts, such as acid addition salts, to the isoelectric point, for example with weak bases, or by treatment with liquid ion exchangers.

Salts can be converted in the customary manner into the free compounds, metal and ammonium salts for example by treatment with suitable acids, and acid addition salts for example by treatment with a suitable base.

Resultant mixtures of stereoisomers can be separated into the individual isomers by methods which are known per se, for example by fractional crystallisation, adsorption chromatography (column or thin-layer chromatography), or other appropriate methods of separation.

The process also comprises those embodiments of the invention in which compounds obtained as intermediates are used as starting materials and the remaining process steps are carried out therewith or in which the process is interrupted at any stage, or starting materials can be used in the form of derivatives or formed during the reaction.

Preferably, the starting materials and reaction conditions are so chosen that the compounds referred to at the outset as being especially preferred are obtained.

The starting materials of the formula II used in accordance with the invention are also novel and also form the subject matter of the invention. They can be prepared for example by oxidative elimination of the methylene group in a compound of the bicyclomycin type of the formula

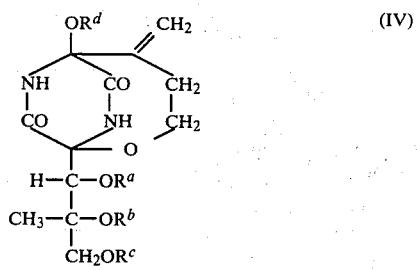

(IV)

wherein $R^a$, $R^b$, $R^c$ and $R^d$ are as previously defined herein, and, if desired, in a resultant compound, introducing or removing one or more hydroxyl protective groups $R^a$, $R^b$, $R^c$ and/or $R^d$ or converting them into other hydroxyl protective groups.

The oxidative elimination of the methylene group can be accomplished in a manner known per se, for example by oxidation with potassium permanganate or by hydroxylation, for example with osmium tetroxide, and subsequent glycol cleavage, for example with periodic acid or lead (IV) salts, the hydroxyl groups of the starting material being preferably protected and optionally subsequently removed. Advantageously, the methylene group is removed by ozonisation, because, among other reasons, unprotected hydroxyl groups are not affected.

The ozonisation can be carried out in a manner known per se, for example by introducing a flow of oxygen which contains ozone into a solution of a bicyclomycin compound in a solvent which is inert to ozone until the theoretical amount of ozone has been consumed, and by decomposing the resultant ozonide thermally or by hydrolysis, reduction or oxidation. Suitable solvents for ozonisation are polyhalogenated, in particular chlorinated, lower alkanes, such as dichloromethane, chloroform and dichloromethane, and in particular lower alkanols, such as methanol and ethanol, lower alkanecarboxylic acids, such as acetic acid, butyric acid, and preferably propionic acid, and the esters thereof with lower alkanols, such as ethyl acetate, as well as mixtures of such solvents. Preferred media are solvents and solvent mixtures which remain liquid even at low temperatures, for example below $-20°$ C. and preferably also below $-50°$ C., and which still retain a good dissolving power for the starting materials to be ozonised. The ozonisation is carried out at decreased temperature, for example between approx. $+10°$ and $-80°$ C., preferably between approx. $-18°$ and approx. $-70°$ C. Normally the reaction is carried out with a small excess of ozone, which can be easily detected by the residual blue colouration of the reaction mixture. The decomposition of the resultant ozonide is effected in the present process preferably by adding dimethyl sulphide, after which the reaction mixture is brought to room temperature. The presence of water, for example of moisture or water of crystallisation, does not affect these reactions.

Free bicyclomycin of the formula IV, wherein $R^a$, $R^b$, $R^c$ and $R^d$ represent hydrogen atoms, is preferably used as starting material for the removal of the methylene group by ozonolysis. However, it is also possible to use corresponding derivatives, for example 1',3',6-tri-tetrahydropyranyl ether, with equal success.

The pharmacologically useful compounds of the present invention can be used, for example, for the manufacture of pharmaceutical preparations which contain an effective amount of the active substance together or in admixture with inorganic or organic solid or liquid pharmacologically useful carriers, which are suitable preferably for enteral or parenteral administration.

Tablets or gelatin capsules are therefore used which contain the active substance together with diluents, for example lactose, dextrose, saccharose, mannitol, sorbitol, cellulose and/or glycin, and lubricants, for example silica, talc, stearic acid or salts thereof, such as magnesium or calcium stearate, and/or polyethylene glycol. Tablets also contain binding agents, for example magnesium aluminium silicate, starches, such as maize, wheat, rice or arrow root starch, gelatin, tragacanth, methyl cellulose, sodium carboxymethyl cellulose and/or polyvinylpyrrolidone, and, if desired, disintegrators, for example starches, agar, alginic acid or a salt thereof, such as sodium alginate, and/or effervescent mixtures, or adsorption agents, colourants, flavouring matters and sweeteners. It is also possible to use the novel pharmacologically active compounds in the form of preparations which can be administered by injection, for example, by intravenous injection, or of infusion solutions. Such solutions are preferably isotonic aqueous solutions or suspensions which can be prepared before use, for example from lyophilised preparations that contain the active substance alone or together with a carrier, for example mannitol.

The pharmaceutical preparations, can be sterilised and/or contain adjuvants, for example preservatives, stabilisers, wetting agents and/or emulsifiers, solubility promoters, salts for regulating the osmotic pressure and/or buffers. The pharmaceutical preparations which, if desired, can contain further pharmacologically useful substances, are manufactured in known manner, for example using conventional mixing, granulating, confectioning, dissolving or lyophilising methods, and they contain from about 0.1% to 100%, especially from about 1% to about 50%, and lyophilisates up to 100% of the active substance. In particular, pharmaceutical preparations are prepared as dosage units. Throughout the description and in the Examples, for the sake of clarity the nomenclature of the corresponding compounds is derived from bicyclomycin [systematic name: 6-hydroxy-5-methylene-(1',2',3'-trihydroxy-2'-methylpropyl)-2-oxa-7,9-diazabicyclo[4,2,2]decane-8,10-dione] or from 5-norbicyclomycin-5-one [systematic name: 6-hydroxy-1-(1',2',3'-trihydroxy-2'-methylpropyl)-2-oxa-7,9-diazabicyclo[4,2,2]decane-5,8,10-trione]as basic substance.

The following Examples will serve to illustrate the invention.

Preparation of the Starting Materials (A) A flow of ozone-enriched oxygen is introduced at $-70°$ C. at a speed of approx. 20 liters/hr into a solution of 8 g of bicyclomycin monohydrate in 350 ml of methanol. After about 45 minutes, when a permanent blue colouration ensues, 2.2 ml of dimethyl sulphide are added and the reaction mixture is brought gradually to $0°$ C. The crystallised product is collected with suction and the mother liquor is concentrated to about a third of its volume and allowed to stand in order to obtain the second crop of crystals of the same quality. The resultant 5-nor-bicyclomycin-5-one has a melting point of $160°-162°$ C., which rises to $171°-175°$ C. after crystallisation from ethyl acetate-methanol.

(B) A solution of 11.5 g of bicyclomycin-6,1',3'-tri-tetrahydropyranyl ether in 200 ml of methanol is ozonised as described in (A) and treated with dimethyl sulphide. After it has warmed to room temperature, the reaction mixture is concentrated and the residue dissolved in a very small amount of ether. The solution is added dropwise into petroleum ether and the white amorphous precipitate is collected with suction and dried in a high vacuum. The resultant 5-nor-bicyclomycin-5-one-6,1',3'-tri-tetrahydropyranyl ether melts unsharp between 65° to 75° C.

(C) 3 g of bicyclomycin-3'-benzoate in methanolic solution are ozonised under the conditions of (A). The excess ozone is destroyed with dimethyl sulphide and the solution is concentrated in a water jet vacuum. The residue is precipitated from methanol with ethyl acetate and yields amorphous 5-nor-bicyclomycin-5-one-3'-benzoate with a melting point of 125°-130° C.

EXAMPLE 1

A mixture of 2.43 g of 5-nor-bicyclomycin-5-one in 160 ml of ethanol and 0.75 ml of pyridine is treated with 0.56 g of hydroxylamine hydrochloride and heated, with stirring, to 60° C. until, after approx. 1 hour, thin-layer chromatography reveals that no more starting material is present. The reaction mixture is concentrated and chromatographed over 100 g of silica gel. The product is eluted with a 1:1 mixture (v/v) of chloroform and methanol and crystallised from methanol. Additional crystallisation from methanol/ethyl acetate affords 5-hydroxy-imino-5-nor-bicyclomycin, which melts at 185°-187° C. (with decomposition); $[\alpha]_D = +19 \pm 1°$ (c=0.95; water).

EXAMPLE 2

Following the procedure described in Example 1, a mixture of 18.24 g of 5-norbicyclomycin-5-one, 5.02 g of O-methylhydroxylamine hydrochloride, 5 ml of pyridine and 1250 ml of ethanol is stirred for 30 minutes at 60° C. and worked up. The crude product is obtained by chromatography over 300 g of silica gel and elution with a 4:1 mixture (v/v) of chloroform/methanol. Recrystallisation from methanol/ethyl acetate gives 5-methoxyimine-5-nor-bicyclomycin with a melting point of 165°-168° C.

EXAMPLE 3

Following the procedure described in Example 1, a mixture of 1.824 g of 5-norbicyclomycin-5-one, 0.957 g of O-benzylhydroxylamine hydrochloride, 0.5 ml of pyridine and 120 ml of ethanol is stirred for 1 hour at 60° C. and worked up. The crude product is obtained by chromatography over 100 g of silica gel and elution with a 4:1 mixture (v/v) of chloroform/methanol. Recrystallisation from ethyl acetate gives 5-benzyloxyimino-5-nor-bicyclomycin with a melting point of 108°-110° C.; $[\alpha]_D = +18 \pm 1°$ (c=1.1; dioxane).

EXAMPLE 4

Following the procedure described in Example 1, a mixture of 0.608 g of 5-nor-bicyclomycin-5-one, 0.283 g of O-methoxy-carbonylmethylhydroxylamine hydrochloride, 0.65 ml of pyridine and 40 ml of ethanol is stirred for 1 hour at 50° C. and pH 7-8 and further worked up. The crude product is obtained by chromatography over 30 g of silica gel and elution with a 4:1 mixture (v/v) of chloroform/methanol. Recrystallisation from ethyl acetate gives 5-methoxycarbonylmethoxyimino-5-nor-bicyclomycin with a melting point of 150°-151° C.

EXAMPLE 5

A suspension of 2.43 g of 5-nor-bicyclomycin-5-one and 1.16 g of phenylhydrazine hydrochloride in 0.675 ml of pyridine and 160 ml of ethanol is stirred at room temperature until a clear solution forms and thin-layer chromatography reveals that no more starting material is present. The solution is concentrated in a water jet vacuum and the residue is recrystallised from methanol to give 5-nor-bycyclomycin-5-one phenylhydrazone, which melts at 160° C. (with decomposition); $[\alpha]_D = +76 \pm 1°$ (c=0.97; dioxane); $\lambda_{max} = 282$ and $302\mu$ ($\epsilon = 16300$ and 13300 respectively).

EXAMPLE 6

A clear solution of 0.446 g of semicarbazide hydrochloride in 80 ml of ethanol is treated at 90° C. (bath temperature) with 0.33 ml of pyridine and then with 1.21 g of 5-nor-bicyclomycin-5-one, and the reaction mixture is allowed to stand for 1 hour at this bath temperature. The product, which begins to precipitate in crystalline form while heating, crystallises out completely on cooling and is then collected with suction and washed with a small amount of ethanol. The resultant 5-nor-bicyclomycin-5-one semicarbazone melts with decomposition at 195° C.; $[\alpha]_D = +48 \pm 1°$ (c=0.93; water)

EXAMPLE 7

A mixture of 5.7 g of 5-nor-bicyclomycin-5-one-3'-benzoate and 0.855 g of O-methylhydroxylamine hydrochloride in 0.85 ml of pyridine and 150 ml of ethanol is stirred at 60° C. until, after 3½ hours, thin-layer chromatography reveals that no more starting material is present. The solution is concentrated and the residue is chromatographed over 100 g of silica gel. Elution with a 4:1 mixture (v/v) of chloroform/methanol gives 5-methoxyimino-5-nor-bicyclomycin-3'-benzoate, which is purified by precipitation from a solution of ethylacetate/ether. After it has been dried in a high vacuum, the product melts at 104°-110° C.

EXAMPLE 8

A mixture of 4 g of 5-nor-bicyclomycin-5-one-6,1',3'-tritetrahydropyranyl ether and 0.60 g of O-methylhydroxylamine hydrochloride in 0.576 ml of pyridine and 100 ml of ethanol is stirred at 60° C. until, after 2½ hours, thin-layer chromatography shows that no more starting material is present. The solution is concentrated and the residue, which consists of crude 5-methoxyimino-5-nor-bicyclomycin-6,1',3'-tri-tetrahydropyranyl ether, is dissolved in 30 ml of methanol. Then 20 ml of 50% (v/v) aqueous acetic acid are added and the mixture is stirred for 30 minutes at room temperature and concentrated in a water jet vacuum. The residue is chromatographed over 100 g of silica gel and elution with a 4:1 mixture (v/v) of chloroform/methanol yields a crude product which, after recrystallisation from methanol/ethyl acetate, melts at 165°-168° C. and is identical with the 5-methoxyimino-5-nor-bicyclomycin of Example 2.

EXAMPLE 9

A solution of 1.824 g of 5-nor-bicyclomycin-5-one in 120 ml of ethanol is treated under reflux with 1.125 g of pyridinioacetohydrazide chloride (Girard reagent P). The clear solution is heated for a further 30 minutes and then allowed to cool. After the solution has stood for about 2 hours at room temperature, the product begins to crystallise. Recrystallisation from methanol/ethyl acetate gives the pyridinioacetylhydrazone chloride of 5-nor-bicyclomycin with a melting point of 182°–185° C.

EXAMPLE 10

Following the procedure described in Example 1, a mixture of 1.82 g of 5-nor-bicyclomycin-5-one, 1.31 g of O-carboxymethylhydroxylamine hemihydrochloride, 2 ml of pyridine and 120 ml of ethanol is stirred for 90 minutes at 60° C. and concentrated. The crystallised product is purified by chromatography over silica gel and elution with a 4:1 mixture (v/v) of chloroform/methanol. Recrystallisation from methanol gives 5-carboxymethoxyimino-5-nor-bicyclomycin with a melting point of 160°–163° C.; $[\alpha]_D = +28 \pm 1°$ (c=0.896; water).

EXAMPLE 11

Following the procedure described in Example 1, a mixture of 1.82 g of 5-nor-bicyclomycin-5-one, 0.720 g of O-(2-hydroxyethyl)-hydroxylamine hydrochloride, 120 ml of ethanol and 0.72 ml of pyridine is stirred for $2\frac{1}{4}$ hours and concentrated. The product is purified by chromatography over silica gel and elution with a 4:1 mixture (v/v) of chloroform/methanol. Precipitation from methanol/ethyl acetate yields amorphous 5-(2-hydroxyethoxyimino)-5-nor-bicyclomycin with a melting point of 88°–94° C.; $[\alpha]_D = +19 \pm 1°$ (c=0.644; dioxane).

EXAMPLE 12

Following the procedure described in Example 1, a mixture of 1.82 g of 5-nor-bicyclomycin-5-one, 1.15 g of O-(2-dimethylaminoethyl)-hydroxylamine hydrochloride, 120 ml of ethanol and 2.5 ml of pyridine is stirred for $2\frac{1}{4}$ hours at 50° C. On cooling, the product separates out in crystalline form. Recrystallisation from ethanol gives 5-(2-dimethylamino-ethoxyimino)-5-nor-bicyclomycin hydrochloride with a melting point of 210° C. (with decomposition); $[\alpha]_D = +12 \pm 1°$ (c=1.160; water).

EXAMPLE 13

A mixture of 1.82 g of 5-nor-bicyclomycin-5-one, 0.921 g of dimethylamino-acetohydrazide (Girard reagent D), 120 ml of ethanol and 1 ml of pyridine is heated, with stirring, to reflux. After 20 minutes a crystalline product begins to precipitate. After cooling, the crystals are collected with suction and recrystallised from methanol/ethyl acetate to give dimethylaminoacetohydrazone 5-nor-bicyclomycin-5-one with a melting point of 188° C. (with decomposition); $[\alpha]_D = +31 \pm 1°$ (c=1.00; water).

EXAMPLE 14

Following the procedure described in Example 1, a mixture of 1.82 g of 5-nor-bicyclomycin-5-one, 1.11 g of tosylhydrazide (p-toluenesulphonic acid hydrazide) and 100 ml of ethanol is heated for 4 hours to 50° C. and thereafter concentrated. The product is purified by chromatography over silica gel and elution with a 4:1 mixture (v/v) of chloroform/methanol. Recrystallisation from methanol gives 5-nor-bicyclomycin-5-one tosylhydrazone with a melting point of 185°–186° C. (with decomposition); $[\alpha]_D = +33 \pm 1°$ (c=1.001; water).

EXAMPLE 15

Following the procedure described in Example 1, a mixture of 1.82 g of 5-nor-bicyclomycin-5-one, 1.1 g of isonicotinohydrazide (4-pyridine carbohydrazide) and 60 ml of ethanol is heated for 4 hours to 50° C. and thereafter concentrated. The product is purified by chromatography over silica gel and elution with a 2:1 mixture (v/v) of chloroform/methanol, affording the 4-pyridinecarbohydrazone of 5-nor-bicyclomycin-5-one with a melting point of 161°–165° C. (with decomposition; $[\alpha]_D = +19 \pm 1°$ (c=0.889; water).

EXAMPLE 16

A solution of 2.73 g of 5-nor-bicyclomycin-5-one and 1.04 g of ethyl carbazate ($H_2N.NH.CO.OC_2H_5$) in 60 ml of dioxane is treated with 0.15 ml of acetic acid and stirred for 7 hours at 60° C. The reaction mixture is concentrated in vacuo and the residue is chromatographed over silica gel and elution is effected with a 4:1 mixture (v/v) of chloroform/methanol, giving the amorphous ethoxycarbohydrazone of 5-nor-bicyclomycin-5-one with a melting point of 140°–143°; $[\alpha]_D = +34 \pm 1°$ (c=1.017; water).

EXAMPLE 17

A mixture of 2 ml of isobutyl chloroformate and 20 ml of tetrahydrofurane is added dropwise in the course of 20 minutes to a vigorously stirred solution of 2 g of 5-methoxyimino-5-nor-bicyclomycin in 30 ml of pyridine which has been cooled to −15° C. The mixture is subsequently stirred for $\frac{1}{2}$ hour at −10° C. and then the precipitated pyridine hydrochloride is removed by filtration. The residual solution is concentrated in a high vacuum. Chromatography of the residue over silica gel with chloroform/methanol 19:1 as eluant yields two components: the more rapidly eluted 5-methoxyimino-5-nor-bicyclomycin 1',3'-carbonate and the more slowly eluted amorphous 3'-O-isobutyloxycarbonyl-5-methoxyimino-5-nor-bicyclomycin; $[\alpha]_D = +39 \pm 1°$ (c=0.725; dimethyl sulphoxide).

We claim:

1. A 2-oxa-7,9-diazabicyclo[4,2,2]-decane derivative, which is selected from the group consisting of the following compounds: 5-benzyloxyimino-5-nor-bicyclomycin; 5-carboxymethoxyimino-5-nor-bicyclomycin; 5-methoxyimino-5-nor-bicyclomycin-6,1',3'-tri-tetrahydropyranyl ether; 5-nor-bicyclomycin-5-one phenylhydrazone, 5-nor-bicyclomycin-5-one semicarbazone, and 5-nor-bicyclomycin-5-one pyridinioacetylhydrazone chloride.

2. 5-Hydroxyimino-5-nor-bicyclomycin.

3. 5-Methoxyimino-5-nor-bicyclomycin.

4. 5-Methylcarbonylmethoxyimino-5-nor-bicyclomycin.

5. 5-Methoxyimino-5-nor-bicyclomycin-3'-benzoate.

6. Pharmaceutically tolerable non-toxic salts of compound of claims 1 to 5, provided they contain salt-forming groups.

7. A pharmaceutical preparation useful against bacteria, which contains an effective amount of one of the compound of any one of claims 1 to 6, together with pharmacologically useful carriers.

8. A method of treating anti-bacterial diseases which comprises enteral or parenteral administration of a therapeutically effective dose of a compound according to any one of claims 1 to 6.

9. A method of treating anti-bacterial diseases which comprises enteral or parenteral administration of a therapeautically effective dose of a pharmaceutical preparation according to claim 7.

* * * * *